United States Patent [19]

Berger et al.

[11] Patent Number: 5,242,802
[45] Date of Patent: Sep. 7, 1993

[54] PROCESSES FOR THE STABILIZATION OF PROSTATE SPECIFIC ANTIGEN IN NATURAL MATRICES

[75] Inventors: Tina S. Berger; Linda P. Ivor, both of San Diego, Calif.

[73] Assignee: Hybritech Incorporated, San Diego, Calif.

[21] Appl. No.: 780,841

[22] Filed: Oct. 23, 1991

Related U.S. Application Data

[63] Continuation of Ser. No. 103,766, Oct. 1, 1987, abandoned, which is a continuation of Ser. No. 717,345, Mar. 29, 1985, abandoned.

[51] Int. Cl.$^5$ ............... G01N 33/543; G01N 33/574
[52] U.S. Cl. .................... 435/7.9; 435/7.23; 435/7.94; 435/962; 435/963; 436/518; 436/536; 436/548; 436/813; 436/825
[58] Field of Search .......... 435/7.23, 7.94, 962, 435/963, 7.9; 436/8, 16, 18, 175, 518, 536, 548, 825, 813

[56] References Cited

U.S. PATENT DOCUMENTS

| | | | |
|---|---|---|---|
| 3,689,633 | 9/1972 | Sanae et al. | 436/825 X |
| 4,007,008 | 2/1977 | Becker et al. | 424/101 |
| 4,056,608 | 11/1977 | Ullman et al. | 436/825 |
| 4,180,556 | 12/1979 | Kim et al. | 436/825 X |
| 4,208,400 | 6/1980 | Edwards | 436/825 |
| 4,362,531 | 12/1982 | de Steenwinkel et al. | 436/512 |
| 4,446,122 | 5/1984 | Chu et al. | 436/518 |
| 4,455,381 | 6/1984 | Magnusson et al. | 436/825 |
| 4,459,359 | 7/1984 | Neurath | 436/507 |
| 4,483,922 | 11/1984 | Carpenter et al. | 435/184 |
| 4,657,851 | 4/1987 | Feller et al. | 436/174 |
| 4,690,890 | 9/1987 | Loor et al. | 436/548 |
| 4,703,001 | 10/1987 | Vodian et al. | 435/5 |

FOREIGN PATENT DOCUMENTS 8300023 1/1983 PCT Int'l Appl. .

OTHER PUBLICATIONS

Wong, *Clinical Chemistry,* 21, 216-220, 1975.
Catherwood et al, *Biomedicine and Pharmacotherapy,* 38, 235-241, 1984.
Heath III et al, *Biomedicine and Pharmacotherapy,* 38, 241-245, 1984.
Chu et al, *Annals New York Acad. Sci.,* 417, 383-389, 1983.

*Primary Examiner*—David Saunders
*Attorney, Agent, or Firm*—Campbell & Flores

[57] ABSTRACT

Processes for preparing stable natural matrices for prostrate specific antigen (PSA) are disclosed. Biological carrier fluids for PSA obtained from a suitable mammal are modified to inhibit the activity of components of the biological fluids destabilizing to PSA. The stable natural matrices, prepared in accordance with the present invention, are useful in the measurement of PSA in a sample by means of an immunoassay.

4 Claims, No Drawings

PROCESSES FOR THE STABILIZATION OF PROSTATE SPECIFIC ANTIGEN IN NATURAL MATRICES

This application is a continuation of U.S. Ser. No. 07/103,766, filed Oct. 1, 1987, now abandoned, which in turn is a continuation of U.S. Ser. No. 06/717,345, filed Mar. 29, 1985, now abandoned, the contents of which are hereby incorporated by reference into the present disclosure.

FIELD OF THE INVENTION

This invention relates to the detection and quantitation of antigenic substances in fluids such as serum. More particularly, it relates to processes for preparing stable natural matrices for use in immunoassays for prostate specific antigen.

BACKGROUND OF THE INVENTION

Prostate specific antigen (PSA), a well characterized tumor associated antigen, is a significant diagnostic and prognostic marker in human prostatic carcinoma. As prostate tumor cells release PSA into the bloodstream, PSA concentrations in serum and other body fluids correlate with the progression of primary or metastatic carcinoma. Accordingly, the quantitation of PSA in patient specimens provides clinicians with an effective means of monitoring a therapeutic regimen and evaluating remission or progression of the disease state.

Present immunoassays for the measurement of PSA in patient fluid samples, such as the immunoradiometric assay (IRMA) and the enzyme-linked immunosorbent assay (ELISA), rely on the use of artificial or synthetic matrices, such as bovine serum albumin, as calibrator matrices and as diluents. As used herein, the term "calibrator matrix" refers to a matrix in which predetermined concentrations of an antigenic substance may be maintained for the calibration of unknown concentrations of the antigenic substance in patient samples. The term "diluent," as used herein, refers to a matrix for dilution of patient samples having concentrations of an antigenic substance which exceed the range of the immunoassay, permitting measurement of the antigenic substance within the immunoassay range.

These matrices are used because unmodified natural matrices, such as serum-based matrices, are rendered unsuitable for use as a result of the instability of PSA upon introduction into such matrices. Specifically, it has been shown that a 30-70% loss of PSA activity occurs within 24 hours after introduction into unmodified human serum-based matrices. Further, this resultant loss of measurable PSA is not limited to human serum since PSA is also unstable upon introduction into bovine and equine serum-based matrices as well.

Because of the dissimilarity of components of such matrices to specimen components, the kinetic patterns on non-specific binding characteristics of artificial matrices may deviate significantly from serum or other body fluids containing, or suspected of containing PSA. As a result, use of these matrices is inherently a substantial limitation to immunoassays for PSA.

Accordingly, to maximize the accuracy and sensitivity of immunoassays for PSA, it is essential that matrices for calibration and sample dilution be as nearly like patient specimens, particularly with respect to non-specific binding characteristics as possible.

Accordingly, there exists a need for means by which PSA may be stabilized in natural matrices, such as serum-based matrices, for use in the quantitative determination of PSA in patient specimens.

SUMMARY OF THE INVENTION

The present invention provides processes for the stabilization of prostate specific antigen (PSA) in natural matrices. In that regard, we have unexpectedly found that natural matrices having kinetic patterns and non-specific binding characteristics similar to those of patient specimens can be modified so that PSA is stable therein without substantially altering their desirable properties as matrices.

According to the present invention, therefore, biologic fluid obtained from a suitable mammal and having kinetic patterns and non-specific binding characteristics the same or substantially the same as the patient sample is modified to inhibit the activity of components of the fluid destabilizing to PSA. In a preferred process of the invention, such biological fluid is modified by an alkaline pH shift from normal (about pH 7) to at least about pH 9 for a period of time effective to inhibit the activity of fluid components destabilizing to PSA. Thereafter, the pH of the biological fluid is decreased to about pH 7.

This invention has been summarized in order that the detailed description that follows may be better understood, and in order that the contribution to the art may be better appreciated.

DETAILED DESCRIPTION OF THE INVENTION

As indicated above, the present invention provides a means by which natural matrices may be modified to stabilize prostate specific antigen (PSA). In the context of the present invention, the term "natural matrix" refers to a biologically occurring composition produced by living processes having kinetic patterns and non-specific binding characteristics the same as, or similar enough to, a patient sample to permit its use as a matrix. The present invention is useful for the detection and/or quantitative measurement of PSA in patient fluid samples by means of conventional immunoassay procedures. More specifically, stable natural matrices prepared in accordance with the processes of the present invention are useful as calibrator matrices and diluents in immunoassays for PSA.

Immunoassays for the determination of concentrations of antigenic substances in fluid samples are well known to the art and need not be described in detail. However, among the immunoassays for which the present invention is particularly useful may be mentioned monoclonal antibody-based immunometric assays, such as the "two-site" or "sandwich" immunometric assays described in U.S. Pat. No. 4,376,110. Additionally, among the means by which such immunoassays may be accomplished may be mentioned radiometric means, enzymatic means and fluorometric means.

In accordance with the present invention, a biological fluid obtained from a suitable mammal is utilized. For example, whole blood, serum, plasma, cerebral spinal fluid or urine may be suitably utilized in the present invention. Preferred for use is serum derived from human blood in which the presence of circulating PSA, if any, is not detectable in significant concentrations. Particularly preferred for use is serum derived from human female blood due to the absence of circulating PSA.

According to the presently preferred process of the present invention, human female serum is modified to inhibit the activity of serum components which destabilize PSA. While Applicant does not intend to be bound by any theory for the instability of PSA in unmodified serum, it is believed that such instability is attributable at least in part to the presence of circulating prostate antigen binding protein (PABG). PABG, while present in significantly elevated levels in the serum of males diagnosed as having prostatic carcinoma, has also been shown to be present in normal male and female serum. Chu et al., *Annals NYAS*, Vol. 417, pp. 383-389, 1983.

Modification of human female serum to provide a stable serum-based matrix for PSA is accomplished by an alkaline pH shift to a pH of at least about pH 9 for a period of time effective to inhibit the activity of serum components destabilizing to PSA. Preferably, the serum pH is shifted to about pH 12, the serum is incubated for about 5 to about 45 minutes and thereafter the serum pH is decreased to about pH 7. Modification of the serum to effect pH changes in accordance with the present invention may be accomplished by conventional procedures well known to the art.

Additionally, it should be noted that while pH modification is the preferred means for inhibiting the activity of serum components reactive with PSA, chaotropic agents may also be utilized in the present invention. Among the chaotropic agents (i.e., agents which induce disorder to the tertiary structure of a protein) suitable for use in the present invention may be mentioned urea, KBr, KI, KSCN, guanidine and $MgCl_2$. Heat may also be used, i.e., the fluid may be heated and held at an elevated temperature for a sufficient time to inhibit the activity of the serum components. However, we have found that the pH adjustments referred to are most effective for this purpose.

The advantages of stable natural matrices prepared in accordance with the present invention when compared with synthetic matrices are apparent by reference to Table I. As the non-specific binding characteristics of such stable natural matrices are comparable to patient specimens, the sensitivity and accuracy of an immunoassay for PSA is enhanced.

Additionally, the stability of PSA in natural matrices modified in accordance with the present invention renders such matrices highly effective and desirable as calibrator matrices and specimen diluents in immunoassays for PSA. As indicated by Tables II and III, PSA is substantially more stable in such matrices as compared with unmodified natural matrices.

Furthermore, it will be appreciated by those skilled in the art having the benefit of this disclosure that the present invention suggests processes for the stabilization of other antigens which are unstable upon introduction into unmodified natural matrices. For example, we have obtained similar results with the tumor-associated antigen calcitonin.

The present invention may be better understood by reference to the following non-limiting example.

EXAMPLE 1

Preparation of pH Modified Serum

Human female serum, obtained from the Interstate Blood Bank, Memphis, Tenn. and maintained at −20° C., was used to prepare a pH modified natural matrix. 1000 ml of the serum was adjusted to approximately pH 12 by addition of 17-20 ml of 10N NaOH in a vessel fitted with a stirring device. The basic serum solution was thereafter incubated for 30 minutes at 22°-28° C. with stirring, followed by a return to approximately pH 7.0 by the addition of 15-17 ml of 10N HCl. The pH 7 solution was thereafter centrifuged for 10 minutes at 1,000×g and filtered through a final sieve of 0.2μ.

Alternate Method for Preparation of pH Modified Serum

Approximately 0.30 ml to 0.50 ml of 10N NaOH was added with stirring to 20 ml of pooled human female serum to increase the pH to 12.0. The basic serum was incubated for 30 minutes followed by addition of 0.1M Sodium Phosphate (0.276 gm monobasic sodium phosphate) with stirring to yield a slight decrease in pH. Thereafter 0.40 ml to 0.60 ml of 6N HCl was added to adjust the pH to pH 6 and the solution was stirred at room temperature for 2-3 hours. The pH was finally adjusted to pH 7 using approximately 0.10 ml to 0.5 ml 1N NaOH.

Comparison of Non-Specific Binding

Non-specific binding values attributable to synthetic matrix samples comprising 5% Bovine Serum Albumin (Miles Laboratories, Inc., Elkhart, Ind.)/2% IgG (Pel-Freeze Biologicals, Rogers, Ark.) were compared with unmodified human female serum samples and pH modified serum samples prepared as described above non-specific binding values were determined using a commercially available two-site immunoradiometric assay, TANDEM®-R PSA (Hybritech Incorporated, San Diego, Calif.). Each matrix was evaluated in a 12 replicate assay using 0.05 ml per tube in accordance with the TANDEM®-R PSA protocol with an extended incubation period of 4 hours.

Table I hereinafter sets forth the average value obtained for the synthetic matrix samples, unmodified serum samples and the pH modified serum samples, respectively. The data is expressed as counts/minute and concentration of PSA (ng/ml) relative to a standard curve.

TABLE I

| Sample Matrix | CPM | PSA (ng/ml) |
| --- | --- | --- |
| 5% BSA/2% IgG | 1179 | 0.24 |
| Unmodified Serum | 930 | 0.07 |
| pH Modified Serum | 946 | 0.09 |

From Table I it is shown that the non-specific binding values obtained for the unmodified and pH modified serum samples were comparable, while the non-specific binding values obtained for the synthetic samples were significantly higher.

Determination of the Stability of PSA

An accelerated stability study of PSA was performed using unmodified human female serum and pH modified serum prepared as described above. A 10 μl quantity of 855 ng/ml PSA from seminal plasma was diluted into 990 μl of each matrix sample and maintained at 35° C. The stability of PSA, set forth in Table II as percent loss of measurable PSA, was determined for each sample at 1, 3 and 5 days relative to a −70° C. control sample. By procedures well known to the art, the values obtained may be extrapolated to 1.2, 3.6 and 6.0 months, respectively at 4° C.

TABLE II

| Sample Matrix | % Loss in Measurable PSA Days at 35° C. | | |
| --- | --- | --- | --- |
| | 1 | 3 | 5 |
| Unmodified | 21 | 32 | 36 |
| pH 12 modified | 4 | 3 | 0 |
| Unmodified | 20 | 26 | 30 |
| pH 12 modified | 8 | 7 | 5 |

From Table II it is readily apparent that PSA was substantially more stable in the pH modified serum as compared with the unmodified serum.

Determination of the Recovery of PSA

The loss of measurable PSA from either seminal plasma or human male serum following dilution into untreated serum or serum modified as described above was determined. Into 4 tubes containing 0.4 ml of sample matrix, 0.1 ml of 125 ng/ml PSA from seminal plasma was added to yield an expected concentration of 25 ng/ml PSA. An aliquot of each solution was then diluted 1:1 into human male serum previously analyzed to contain 19.1 ng/ml PSA. Each of the four tubes were evaluated for PSA content using a commercially available two-site immunoradiometric assay, TANDEM®-R PSA, (Hybritech Incorporated, San Diego, Calif.), with an extended incubation period of 4 hours. The resulting concentrations and calculated percent loss of PSA are shown in Table III. The data clearly indicates a highly desirable recovery of PSA for the pH modified matrix, while significant loss of PSA occurs in unmodified serum.

TABLE III

| | PSA Expected ng/ml | PSA Observed ng/ml | PSA % Loss |
| --- | --- | --- | --- |
| Addition of PSA From Seminal Plasma | | | |
| Unmodified Serum | 25.0 | 12.33 | 51 |
| pH Modified Serum | 25.0 | 24.16 | 3 |
| Dilutions of Solutions 1:1 with Human Serum Containing PSA | | | |
| Unmodified Serum | 15.72 | 15.29 | 3 |
| pH Modified Serum | 21.63 | 22.17 | 0 |

The foregoing description has been directed to preferred embodiments of the invention in accordance with the requirements of the Patent Statutes for purposes of illustration and explanation. It will be apparent, however, to those skilled in the art that modifications and changes will be possible without departing from the spirit and scope of the invention. It is intended that the following claims be interpreted to embrace all such modifications and changes.

What is claimed is:

1. A process for assaying prostate specific antigen (PSA) in a fluid sample, comprising:
   a. obtaining a mammalian biological carrier fluid being substantially free from circulating PSA, said fluid also containing components destabilizing to PSA;
   b. modifying the carrier fluid by increasing the pH of the biological fluid to at least about pH 9 for a period of time effective to inhibit the activity of components of the biological fluid destabilizing to said PSA and thereafter decreasing the pH to about 7 to form a stable natural matrix;
   c. adding the fluid sample to the stable natural matrix; and
   d. determining the presence or concentration of PSA by an immunoassay.

2. The process according to claim 1 wherein said immunoassay is a monoclonal antibody-based immunometric assay.

3. The process according to claim 2 wherein said immunoassay is a "two-site" immunometric assay.

4. The process according to claim 2, wherein the measurement of PSA in said immunometric assay is accomplished by means selected from the group consisting of radiometric means, enzymatic means and fluorometric means.

* * * * *